| United States Patent [19] | [11] Patent Number: 5,007,923 |
| --- | --- |
| Bezwada et al. | [45] Date of Patent: Apr. 16, 1991 |

[54] CRYSTALLINE COPOLYESTERS OF AMORPHOUS (LACTIDE/GLYCOLIDE) AND P-DIOXANONE

[75] Inventors: Rao S. Bezwada, Whitehouse Station; Hugh D. Newman, Jr., Chester; Shalaby W. Shalaby, Lebanon, all of N.J.

[73] Assignee: Ethicon, Inc., Somerville, N.J.

[21] Appl. No.: 472,990

[22] Filed: Jan. 31, 1990

[51] Int. Cl.$^5$ .................... A61B 17/00; C08G 63/00
[52] U.S. Cl. .................... 606/231; 606/230; 528/354; 525/411; 525/415
[58] Field of Search .............. 606/230, 231; 525/411, 525/415; 528/354

[56] References Cited

U.S. PATENT DOCUMENTS

| | | | |
| --- | --- | --- | --- |
| 4,052,988 | 10/1977 | Doddi et al. | 606/231 |
| 4,402,445 | 9/1983 | Green | 606/220 |
| 4,428,376 | 1/1984 | Mericle | 606/220 |
| 4,643,191 | 2/1987 | Bezwada et al. | 606/231 |
| 4,646,741 | 3/1977 | Smith | 606/220 |
| 4,653,497 | 3/1987 | Bezwada et al. | 606/230 |

OTHER PUBLICATIONS

R. S. Bezwada et al, Bioabsorbable Copolymers of Poly-Dioxanone: Effect of Composition & Microstructure on Physical & Biological Properties of Copolmeric P-Dioxanone/Glycolide Fibers, Ethicon, Inc, Catalog.
J. A. Ray et al, Polydioxanone (PDS), a Novel Monofilament Synthetic Absorbable Suture, Surg., Gynecology & Obstetrics, 10-1981, vol. 153 pp. 497–507.
Ronald W. Hoile, The use of a new suture material (polydioxanone) in biliary tract; Instruments and Techniques, pp. 168–171; *no date avail.
J. Elliott Blaydes et al, 9-0 Monofilament Polydioxanone (PDS): A New Synthetic Absorbable Suture for Cataract; Ophthalmic Surgery; Aug. 1982, vol. No. 8.

*Primary Examiner*—Stephen C. Pellegrino
*Assistant Examiner*—Gary Jackson
*Attorney, Agent, or Firm*—Matthew S. Goodwin

[57] ABSTRACT

A crystalline copolyester of p-diaxanone and a prepolymer of lactide and glycolide, and absorbable surgical filaments derived therefrom.

13 Claims, No Drawings

CRYSTALLINE COPOLYESTERS OF AMORPHOUS (LACTIDE/GLYCOLIDE) AND P-DIOXANONE

BACKGROUND OF THE INVENTION

This invention relates to copolyesters derived from p-dioxanone, and especially to such crystalline copolyesters having mechanical and biological properties which are desirable for the preparation of absorbable surgical sutures.

U.S. Pat. No. 4,052,988 describes p-dioxanone homopolymers and the preparation of absorbable filaments exhibiting mechanical and biological properties suitable for use as surgical sutures. Unlike previous absorbable synthetic sutures developed, for example sutures derived from homopolymers of lactide or copolymers of lactide and glycolide, p-dioxanone sutures can be used as a monofilament because of their enhanced flexibility and pliability. Conventional synthetics require a braided or twisted construction in a multifilament form in order to reduce the "stiff" feel of the suture. Unfortunately, multifilament sutures are often disadvantageous because their rough surface can often tear tissue during operative procedures.

As good as the sutures derived from p-dioxanone are, there is still room for improvement. U.S. Pat. No. 4,643,191 describes copolymers of p-dioxanone and lactide, and absorbable sutures prepared therefrom. The lactide component of the copolymer may offer enhanced physical properties, for example, increased straight or knot tensile strength and reduced modulus, without sacrificing any of the other outstanding properties of a p-dioxanone homopolymer.

U.S. Pat. No. 4,653,497 describes absorbable sutures prepared from copolymers of p-dioxanone and glycolide. The glycolide component of the copolymer significantly increases the rate of in vivo absorption and the in vivo breaking strength retention properties of the copolymer, properties which can be extremely advantageous for certain operative procedures.

In view of the attempts described in the art to modify or enhance the properties of p-dioxanone homopolymers, it would be desirable to formulate a polymer composition which can offer the possibility of creating flexibility in the biological properties attained without sacrificing mechanical properties.

SUMMARY OF THE INVENTION

In one aspect, the invention is a crystalline copolyester of p-dioxanone and an amount of an amorphous prepolymer of lactide and glycolide effective to modify the in vivo breaking strength retention and in vivo absorption profile of the copolyester relative to the in vivo breaking strength retention and in vivo absorption profile of a p-dioxanone homopolymer.

In another aspect, the invention is an absorbable surgical filament prepared by melt spinning the crystalline copolyester described above.

The crystalline copolyesters of this invention can be readily melt spun using conventional techniques to prepare fibers having the combination of mechanical and biological properties necessary for use as an absorbable, monofilament surgical suture. By varying the ratio of lactide to glycolide in the amorphous prepolymer, or by varying the concentration of prepolymer in the copolyester, the in vivo breaking strength retention and the in vivo absorption profile can be modified significantly without compromising desirable properties relative to that of a p-dioxanone homopolymer. Therefore, the properties of crystalline copolyesters of this invention can be tailored for specific applications.

The copolyesters are useful for the preparation of surgical filaments, especially absorbable, monofilament surgical sutures, although these copolyesters may find use in the preparation of other surgical devices. For example, the copolymers may be used as surgical meshes, surgical staples, hemostatic clips, and the like.

DETAILED DESCRIPTION OF THE INVENTION

In a preferred embodiment, the crystalline copolyesters of this invention have a degree of crystallinity and an intrinsic viscosity which render the copolyesters suitable for extrusion into fibers or films and for injection molding into surgical devices such as staples. Advantageously, the crystallinity of the copolyesters is greater than about 10 percent as measured by x-ray diffraction, so that the copolyesters can maintain its structural integrity at the elevated temperatures required for extrusion and molding. Preferably, the intrinsic viscosity of the crystalline copolyesters ranges from about 0.8 to about 3.0, more preferably from about 1.2 to about 2.0 dl/g in a 0.1 g/dl solution of hexafluoroisopropyl alcohol (HFIP) at 25° C. A copolyester with an intrinsic viscosity below about 0.8 dl/g generally lacks sufficient viscosity to provide suitable melt strength for extrusion or molding, and an intrinsic viscosity above about 3.0 dl/g is generally too viscous for melt processing.

The amount of amorphous lactide/glycolide prepolymer used to prepare the copolyester can vary over a wide range, and will depend to a great extent on the breaking strength retention and absorption properties desired. Typically, an amount ranging from about 5 to about 50 percent by weight of the composition of the polyester is acceptable. An amount less than 5 percent prepolymer generally will not modify the properties of the copolyester relative to a p-dioxanone homopolymer, and amounts greater than 50 percent may adversely affect mechanical properties relative to a p-dioxanone homopolymer. An amount of prepolymer ranging from about 10 to about 20 weight percent is preferred.

The ratio of lactide to glycolide used to prepare the prepolymer must be adjusted so that the resulting prepolymer structure is amorphous. This is important to facilitate the successful copolymerization of the prepolymer with p-dioxanone. Amorphous prepolymers exhibiting the properties desired for copolymerization with p-dioxanone can generally be prepared at a mole ratio of lactide to glycolide as low as 50/50, but a ratio ranging between 60/40 and 70/30 is preferred. Generally, if the amount of glycolide exceeded 50 mole percent of the amorphous prepolymer, then the amorphous prepolymer would have a melting temperature greater than the desired temperature for copolymerizing with p-dioxanone. An amorphous prepolymer prepared from greater than 70 mole percent lactide would typically provide a copolyester exhibiting a slower rate of absorption and a larger retention of breaking strength than desired.

The amorphous prepolymer of lactide and glycolide at varying ratios of lactide to glycolide can be prepared by conventional polymerization techniques well known in the art, for example, as described in U.S. Pat. No. 3,636,956. Once the prepolymer is prepared, the copolyester can be prepared by polymerizing the desired proportions of prepolymer and p-dioxanone in the presence of an organometallic catalyst and an initiator at elevated temperatures. The organometallic catalyst is preferably a tin-based catalyst, e.g. stannous octoate, and is present in the monomer mixture at a mole ratio of monomer to catalyst preferably ranging from 15,000 to 40,000/1. The initiator is typically an alkanol, a glycol, a hydroxyacid, or an amine, and is present in the monomer mixture at a mole ratio of monomer to initiator ranging from 400 to 2000/1. The polymerization can be carried out at a temperature range from 100° to 160° C., preferably 110°-140° C., until the desired molecular weight and viscosity are acheived, but for no longer than 16 hours. Alternatively, the polymerization can be carried out in 2 or more successive stages, for example, for 1-2 hours at 100°-140° C. and then for 2-5 days at about 80° C.

Once the desired copolyester is prepared, filaments exhibiting the requisite properties for use as surgical sutures may be prepared using conventionally accepted methods well known in the art by first melt extruding the copolymer through a spinnerette to prepare fibers, drawing the fibers to create orientation, and then annealing the oriented fibers to enhance dimensional stability. See, for example, U.S. Pat. Nos. 4,643,191 and 4,653,497, which also describe in detail the testing procedures used for determining the mechanical and biological properties of those monofilaments described in the examples.

As the term is used in the claimed invention, the in vivo breaking strength retention (BSR) is a measure of the ability of a fiber to retain its strength after implantation in an animal, typically a rat. It is the ratio of the breaking strength of the fiber after a predetermined period to the breaking strength before implantation. Therefore, the in vivo BSR is modified when the fiber loses its breaking strength after implantation over a shorter or longer period of time relative to the time required for a fiber derived from a p-dioxanone homopolymer to lose its breaking strength after implantation. The procedures for determining the in vivo BSR have been well documented and are described in the patents cited in the preceding paragraph.

The in vivo absorption profile is a profile taken over a period of time of the amount of degradation of a section of a fiber after implantation in a suitable test animal, e.g. a rat. This degradation is measured by calculating the median percent of the original cross-sectional area of the fiber section remaining after an intramuscular implantation for a predetermined number of days. The in vivo absorption profile is modified when the amount of degradation for any given number of days after implantation is greater or less than the amount of degradation after the same period of time for a fiber section derived from a p-dioxanone homopolymer. The procedures for determining the in vivo absorption profile are described in numerous patents, for example, U.S. Pat. No. 4,653,497.

Although the BSR in vivo and the rate of absorption in vivo can be modified significantly to tailor such properties for a specific operative procedure, it is desirable to make such changes without sacrificing mechanical properties. In preferred embodiments, the straight tensile strength of a monofilament prepared from the copolyesters of this invention is greater than 40,000 psi, preferably greater than 50,000 psi, and the knot tensile strength is greater than 30,000 psi, preferably greater than 40,000 psi. Additionally, the Young's Modulus of such a monofilament is less than 500,000 psi, preferably less than 300,000 psi, and the percent elongation is less than 80, preferably less than 60.

The following examples are intended to illustrate preferred embodiments and are in no way intended to limit the scope of the claimed invention. As used in Table 1, PDO, PGA and PLA refer to polymers derived from p-dioxanone, glycolide and lactide, respectively.

EXAMPLE 1

PREPARATION OF COPOLYMER OF L(−) LACTIDE/GLYCOLIDE AT 65/35 BY MOLE

A flame dried, 500 ml, round bottom, single neck flask is charged with 2.97 ml of 1-dodecanol, 140 grams (0.9714 mole) of L(−) lactide, 60 grams (0.5169 mole) of glycolide, and 0.150 ml of stannous octoate (0.33 molar solution in toluene). The contents of the reaction flask are held under high vacuum at room temperature for about 16 hours. The flask is fitted with a flame dried mechanical stirrer and an adapter with a hose connection. The reactor is purged with nitrogen three times before being vented with nitrogen. The reaction flask is heated to 180° C. and maintained there for 30 minutes. The reaction is conducted for 2 hours at 160° C. and for about 16 hours at 110° C.

The prepolymer is isolated, ground, and dried under vacuum at 90° C./16 hours and 110° C./16 hours to remove any unreacted monomers. A weight loss of 0.34% is observed. The resulting copolymer is amorphous and has an inherent viscosity (I.V.) of 0.59 dl/g in HFIP at 25° C.

EXAMPLE 2

PREPARATION OF COPOLYESTER OF LACTIDE/GLYCOLIDE AMORPHOUS PREPOLYMER AND P-DIOXANONE AT 10/90 BY WT.

To a dry, 250 milliliter, single neck, round bottom flask 10 grams of the L(−) lactide/glycolide prepolymer prepared from Example 1 is added. The contents of the flask are dried at 110° under high vacuum (less than 0.05 mm of mercury) for about 16 hours. To the same flask, after cooling to room temperature, 90 grams (0.8816 mole) of dioxanone, and 0.089 ml of stannous octoate solution (0.33 molar in toluene) are charged, and then the flask is dried about 16 hours under high vacuum at room temperature. The flask is fitted with a flame dried mechanical stirrer and an adapter with a hose connection. The mixture is heated to 75°-80° C. under a stream of nitrogen. In order to dissolve the prepolymer in the p-dioxanone monomer, the temperature of the reaction flask is raised to 140° C. briefly before dropping to 110° C. The temperature is maintained at 110° C. for 8 hours. The resulting copolyester is isolated, ground, and dried 48 hours/60°-80° C./0.1 mm Hg to remove any unreacted monomer. A weight loss of 20.6% is observed. The copolyester has a melting range of 102°-108° C. by hot stage microscopy and an inherent viscosity of 2.41 dl/g in HFIP.

EXAMPLE 3

PREPARATION OF COPOLYESTER OF LACTIDE/GLYCOLIDE AMORPHOUS PREPOLYMER AND P-DIOXANONE AT 20/80 BY WT.

The procedure of Example 2 is repeated, except that 80 grams (0.7836) of p-dioxanone, and 0.079 ml of stannous octoate solution (0.33 molar in toluene) are reacted with 20 grams of the L(−) lactide/glycolide prepolymer prepared from Example 1. The resulting copolyester has a melting range of 94°–98° C. by hot stage microscopy and an inherent viscosity of 1.72 dl/g in HFIP.

EXAMPLE 4

PREPARATION OF COPOLYESTER OF LACTIDE/GLYCOLIDE AMORPHOUS PREPOLYMER AND P-DIOXANONE AT 10/90 BY WT.

The procedure of Example 2 is substantially repeated. The resulting copolyester has a melting range of 102°–110° C. by hot stage microscopy and an inherent viscosity of 2.64 dl/g in HFIP.

EXAMPLE 5

PREPARATION OF COPOLYESTER OF LACTIDE/GLYCOLIDE AMORPHOUS PREPOLYMER AND P-DIOXANONE AT 20/80 BY WT.

The procedure of Example 3 is substantially repeated. The resulting copolyester has a melting range of 96°–100° C., and an inherent viscosity of 1.15 dl/g in HFIP.

EXTRUSION AND DRAWING

The copolyesters of Examples 2–5 are melt extruded and subsequently drawn using standard procedures.

ANNEALING

The drawn monofilaments are annealed and tested. The mechanical and biological properties of the oriented and annealed monofilaments are summarized in Table 1.

TABLE 1

(LACTIDE/GLYCOLIDE)/PDO COPOLYESTERS

| | Example No. 2 | | Example No. 3 | | Example No. 4 | Example No. 5 | Control[1] |
|---|---|---|---|---|---|---|---|
| Initial wt. composition of (lactide/glycolide)[2]/PDO | 10/90 | | 20/80 | | (10)/90 | (20)/80 | — |
| % Conversion | 79.4 | | 82.3 | | 78.5 | 80.0 | — |
| I.V. dl/g | 2.41 | | 1.72 | | 2.64 | 1.15 | 1.88 |
| M.P. (hot stage) | 101–108° C. | | 94–98° C. | | 101–110° C. | 96–102° C. | 109° C. |
| Mole % Composition by NMR PDO/PGA/PLA | — | | 78.7/8.6/12.7 | | 90.0/4.3/5.7 | — | — |
| Fiber Properties (oriented) | | | | | | | |
| Diameter (mils) | 13.0 | 6.1 | 11.5 | 4.9 | 7.7 | 6.5 | — |
| Str. Tensile, KPSI | 73 | 88 | 79 | 148 | 90 | 80 | — |
| Knot Tensile, KPSI | 38 | 51 | 46 | 79 | 43 | 57 | — |
| Elongation | 54% | 53% | 55% | 60% | 52% | 46% | — |
| Y.M., KSPI | 102 | 127 | 188 | 120 | 109 | 280 | — |
| Properties (annealed) | | | | | 6 hrs/80° C./5% relx. | 6 hrs/80° C./5% relx. | 12 hrs/60° C. |
| Diameter (mils) | 13.01 | 6.03 | 12.51 | 5.98 | 8.05 | 7.34 | 6.6 |
| Str. Tensile, KPSI | 73 | 88 | 67 | 76 | 91 | 54 | 74 |
| Knot-Tensile, KSPI | 38 | 60 | 41 | 49 | 58 | 46 | 55 |
| Elongation | 36% | 37% | 43% | 37% | 30% | 28% | 29% |
| Y.M., KPSI | 150 | 265 | 207 | 284 | 327 | 370 | 324 |
| In Vivo BSR[3], %   3 weeks | | | 62 | | 55 | 39 | 70 |
|                              4 weeks | | | 24 | | 28 | 25 | 50 |
|                              8 weeks | | | 0 | | 0 | 0 | 10 |
| In Vivo Absorption   5 days | | | 100 | | 100 | 100 | 100 |
|                              119 days | | | 36 | | 0 | 0 | 83 |
|                              154 days | | | 0 | | — | 0 | — |
|                              182 days | | | 0 | | 0 | 0 | 73 |

[1]PDS ™ violet monofilament polydioxanone suture
[2]lactide/glycolide at 65/35 by mole
[3]Determined according to procedures described in U.S. Pat. No. 4,653,497

The data from Table 1 shows that by varying the ratio of lactide to glycolide or the concentration of prepolymer in the copolyester, the in vivo BSR and in vivo absorption profile can be modified relative to the in vivo BSR and in vivo absorption profile of a p-dioxanone homopolymer, without compromising mechanical properties. In these particular examples, the copolyesters exhibit a decreased in vivo BSR and a faster in vivo absorption relative to that of the p-dioxanone homopolymer.

Although the examples presented described experiments using a specific mole ratio of lactide to glycolide and a narrow range of concentrations for the prepolymer in the copolyester, similar excellent results may be obtained by varying the ratio of lactide to glycolide and the concentration of prepolymer within the scope of the claimed invention taught in this specification. For example, monofilaments can be prepared having the following properties: (1) comparable or improved mechanical properties (particularly compliance) relative to a p-dioxanone homopolymer, (2) an intermediate in vivo BSR between a p-dioxanone homopolymer and a glycolide homopolymer, and (3) an in vivo absorption profile approaching that of a glycolide homopolymer.

We claim:

1. A crystalline copolyester of p-dioxanone and an amount of an amorphous prepolymer of lactide and glycolide effective to modify the in vivo breaking strength retention and in vivo absorption profile of the copolyester relative to the in vivo breaking strength retention and in vivo absorption profile of a p-dioxanone homopolymer.

2. The crystalline copolyester of claim 1 wherein the crystallinity of the copolymer is greater than about 10 percent as measured by x-ray diffraction.

3. The crystalline copolyester of claim 2 wherein the intrinsic viscosity of the copolymer ranges from about 1.2 to about 2.0 dl/g.

4. The crystalline copolyester of claim 1 wherein the amount of prepolymer ranges from about 5 to about 50 weight percent.

5. The crystalline copolyester of claim 4 wherein the amount of prepolymer ranges from about 10 to about 20 weight percent.

6. The crystalline copolyester of claim 5 wherein the mole ratio of lactide to glycolide ranges from about 60/40 to about 70/30.

7. An absorbable surgical filament prepared by melt spinning the crystalline copolyester of claim 1 or 6.

8. The surgical filament of claim 7 wherein the filament exhibits a straight tensile strength greater than 40,000 psi and a knot tensile strength greater than 30,000 psi.

9. The surgical filament of claim 8 wherein the filament exhibits a straight tensile strength greater than 50,000 psi and a knot tensile strength greater than 40,000 psi.

10. The surgical filament of claim 9 wherein the filament exhibits a Young's Modulus less than 500,000 psi and an elongation less than 80 percent.

11. The surgical filament of claim 10 wherein the filament exhibits a Young's Modulus less than 300,000 psi and an elongation less than 60 percent.

12. The surgical filament of claim 11 wherein the filament is in the form of a monofilament.

13. The surgical filament of claim 12 wherein the filament is in the form of a suture.

* * * * *